United States Patent [19]

Ornstein

[11] Patent Number: 4,545,831
[45] Date of Patent: Oct. 8, 1985

[54] METHOD FOR TRANSFERRING A THIN TISSUE SECTION

[75] Inventor: Leonard Ornstein, White Plains, N.Y.

[73] Assignee: The Mount Sinai School of Medicine, New York, N.Y.

[21] Appl. No.: 417,307

[22] Filed: Sep. 13, 1982

[51] Int. Cl.[4] .................... G01N 1/00; G01N 33/48; A61K 31/74; B44C 1/16

[52] U.S. Cl. .................................. 156/57; 156/241; 156/307.7; 156/275.5; 156/236; 424/3; 424/81

[58] Field of Search ............... 424/81, 3; 428/13, 913, 428/40, 41, 42; 427/4, 2, 54.1; 156/57, 230, 236, 241, 249, 246, 275.5, 298, 300, 344, 331.7, 331.8, 100, 145, 307.7; 204/159.19, 159.23

[56] References Cited

U.S. PATENT DOCUMENTS

| 3,324,014 | 6/1967 | Modjeska | 156/236 |
| 3,450,613 | 6/1969 | Steinberg | 427/2 |
| 4,120,991 | 10/1978 | Ornstein et al. | 156/57 |
| 4,287,255 | 9/1981 | Wong et al. | 428/913 |
| 4,300,968 | 11/1981 | Föttinger et al. | 427/54.1 |
| 4,320,157 | 3/1982 | von Hagens | 428/13 |

FOREIGN PATENT DOCUMENTS 55-5481  2/1980  Japan .

OTHER PUBLICATIONS

Wedeen and Jernow, *Am. J. Physiol.*, vol. 214, p. 776 (1968 ed.).
Chem. Abstr. 93: 73180p, Tokubuchi et al.
*Nature:* vol. 174, p. 46 (1954); vol. 184, p. 1584 (1959); vol. 190, p. 424 (1961).
Technical Publication No. TA1-0225-10, Jun. 1977, Technicon Instruments Corporation.

*Primary Examiner*—Edward Kimlin
*Assistant Examiner*—Louis Falasco
*Attorney, Agent, or Firm*—Edward H. Gorman, Jr.

[57] ABSTRACT

A method is described for transferring a thin tissue section affixed to a substrate by a first pressure-sensitive adhesive layer to a microscope slide which supports a second pressure-sensitive adhesive layer of polymerizable material. The tissue section is contacted to the second adhesive layer to form a laminate. Following polymerization of the second layer to form a positive bond between the tissue section and microscope slide, the substrate and first adhesive layer are completely removed to expose the tissue section, now affixed to the microscope slide by the polymerized second adhesive layer, for subsequent processing.

15 Claims, 6 Drawing Figures

METHOD FOR TRANSFERRING A THIN TISSUE SECTION

BACKGROUND OF THE INVENTION

1. Field of the Invention

The present invention relates to method for the handling of especially fragile tape-supported thin sections of tissue specimens prior to staining and mounting processes and, more particularly, to expedite and simplify the positive, safe transfer to and support of such sections on microscope slides for such processes.

2. Brief Description of the Invention

Very thin slices of animal and plant tissues are prepared for many diferent kinds of microscopic studies by sectioning with a microtome. While the tissue may be cut fresh, the soft and compliant nature of most fresh tissue makes the cutting of undistorted thin sections very difficult. Often, the tissue is cut on a freezing microtome or in a cryostat at temperatures below 0° C. (32° F. ), the hardness of the frozen water within the tissue allowing sections as thin as a few micrometers to be cut relatively easily. As these frozen sections are brittle and friable, they are difficult to handle and process further. To simplify sectioning of tissue, a number of procedures have been developed which produce a block of supported tissue which has superior sectioning properties and produce high quality, relatively easy-to-handle tissue sections. Such procedures typically involve: (1) Fixation of the tissue in a solution which insolubilizes and hardens the natural polymers of which tissue cells are composed; (2) dehydration of the tissue through a series of water-miscible (e.g. an alcohol) and then paraffin or plastic-monomer-miscible (e.g., toluene or xylene) solvents; (3) infiltration of the tissue by melted paraffin or monomer solution; and (4) embedding by freezing the paraffin or polymerizing the monomer to form a solid polymer. Reference is made to *Staining Methods*, J. F. A. McManus and R. W. Mowry (P. B. Hoeber, Inc., N.Y. 1960) and to *Techniques for Electron Microscopy*, D. Kay, Ed. (Blackwell Sci. Publ., Oxford, England, 1965) pp. 166–212.

However, there are occasional specimens which remain difficult to section. As the section is cut from the tissue, parts of the cut section tend to fragment and fall from the cut section, or fall from the section as it is removed from the microtome. Reference is made to the following which describe procedures for facilitating the cutting and handling such difficult-to-cut tissue sections:

1. A. Palmgren, *Nature*, Vol. 174, p. 46, (1954) describes the use of a pressure-sensitive adhesive tape as a sectioning aid for the cutting of very large, hard or brittle specimens. A piece of adhesive tape is applied to the surface of a specimen, either frozen or embedded in a paraffin block, supported in a microtome. Thus, the section, when cut, is thus supported by the applied tape. The quality of the uncompressed section of hard, brittle and friable tissue thus produced can be far superior to that of a conventional section of the same block of tissue. However, following Palmgren, processing such a section while it remains on the tape, or transferring it to a glass slide (to permit it to be processed thereafter in conventional fashion) involved elaborate, timeconsuming and inconvenient methods which can also damage the section.

2. W. E. Beckel, *Nature*, Vol. 184, p. 1584 (1959) describes the use of Scotch brand No. 810 cellulose-acetate-backed adhesive tape in the process described by Palmgren above. The tape-mounted sections were applied, section-side down on wet conventionally albuminized glass slides. After thorough drying, which requires at least a few hours, the adhesive backing, the adhesive layer and the paraffin were all dissolved in tetrahydrofuran for 30 minutes, leaving only the section adhering to the glass slide and available for further processing by conventional techniques. Alternatively, chloroform for 2 minutes, followed by xylene for 30 minutes, can be used for dissolving the adhesive backing, the adhesive layer and the paraffin. Beckel also described a "more rapid method" which used a film of albumin and a solution of 2 per cent celloidin in methyl benzoate or ethyl alcohol to "cement" the section to the glass slide, followed by 1 minute in chloroform and 10 minutes in xylene to complete the treatment.

3. D. S. Gowers and R. E. Miller *Nature*, Vol. 190, p. 425 (1961) attempted to repeat Beckel's method but found that, with available Scotch brand No. 810 tape, the adhesive could not be dissolved, and with the best alternate available tape, Tuck brand No. 200, safe removal of the tape without damaging the section in solvent took from 1 to 10 hours.

4. R. P. Wedeen and H. I. Jernow *Am. J. Physiol.*, Vol. 214, p. 776, (1968) used cyanoacrylate (Eastman 910 "superglue" ) to attach adhesive-tape-supported frozen sections to radioautographic (photographic) plates. The cyanoacrylate is initially liquid, but polymerizes to a solid when pressed into a thin film. As the cyanoacrylate polymer is soluble in xylene and other processing solvents which would cause the section to float free, it is not useful for conventional staining procedures.

The present invention deals, at least in part, with the mounting of adhesive-tape-supported, cut-tissue sections by permanent bonding to a microscope slide by a rapid and convenient method, the bonding material being such as not to be affected by or interfere with any of the treating processes to which such section is subsequently subjected or with the subsequent microscopic examination of the fully-treated section.

SUMMARY OF INVENTION

To achieve heretofore unavailable advantages which expedite and simplify the processing of tape-mounted tissue sections, the present invention provides a method whereby a tissue section supported on a flexible piece of pressure-sensitive adhesive tape, is contacted with a microscope slide over whose contacting surface a film of pressuresensitive adhesive capable of further polymerization has been layered. Techniques by which flexible tape can be applied to tissue specimens to aid sectioning have been described, for example, in the above-identified publications by Palmgren, Beckel, Gowers et al and Wedeen et al, respectively. After the tissue section has been contacted with the polymerizable layer, the layer is then polymerized, within 1 to 3 minutes, the tape is submerged in a solvent which weakens the supporting tape backing and/or supporting-tape adhesive-layer which are washed or peeled away, to fully expose the tissue section within one additional minute. The polymerizable layer and its bonds to the section have sufficient strength after curing to allow peeling of insoluble tape backing without damaging the section and to thereafter firmly support the section on the microscope slide.

The polymerizable layer can be further characterized, as having only curable components whose respective diffusion coefficients before and during cure are sufficiently low, such that the diffusion thereof into the section during the curing process is minimal, and a viscosity sufficiently large, such that flow into the tissue section on application of finger-pressure is minimal, that is, less than 1 micrometer in 30 minutes. However, when cured, such layer forms a positive bond between the microscope slide and tissue section, to permit ease of handling during subsequent processing of the supported section. As diffusion and flow into the section is minimal, the substantially entire interior structure of the tissue section remains exposable for subsequent to processing. Also, the polymerized bonding layer is not affected, in any way, by such processing.

Significantly, the polymerized layer has a refractive index matched to the refractive index of the unstained tissue, e.g., from about 1.53 to 1.57, and to the mounting medium conventionally used to envelop and to attach the coverslip over the specimen at the completion of the processing. Conventionally, the tissue section is stained during processing to highlight particular components thereof. As the respective refractive indices of the various components of the completed microscope slide are substantially the same, there is no optical interference introduced to degrade the image in the subsequent microscopic examintion of the tissue.

Accordingly, the present invention provides method for positively attaching a tissue section to a microscope slide by a pressuresensitive polymerizable layer, the curable components of such layer prior to and during polymerization penetrating only very minimally into such specimen and, when polymerized, having a compatible index of refraction and neither affecting nor being affected by any subsequent chemical or physical treatment of the supported tissue section.

DETAILED DESCRIPTION OF THE INVENTION

Figure 1:
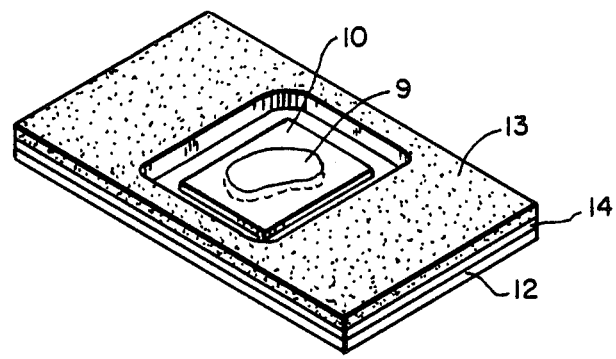
FIG. 1 is an isometric view of a thin tissue section supported on the surface of a flexible tape or substrate.

As indicated in FIG. 1, a thin tissue section 9 surrounded and infiltrated with paraffin 10 is supported on and adhered to the surface of a flexible tape or substrate 12, by a pressure sensitive adhesive layer 14. Section 9 is located within a window or opening in a spacer 13 adhered to layer 14. As described in U.S. Ser. No. 06/354,837, filed on Mar. 4, 1982, spacer 13 facilitates the cutting of a thin section 9 by a microtome.

Figure 2:
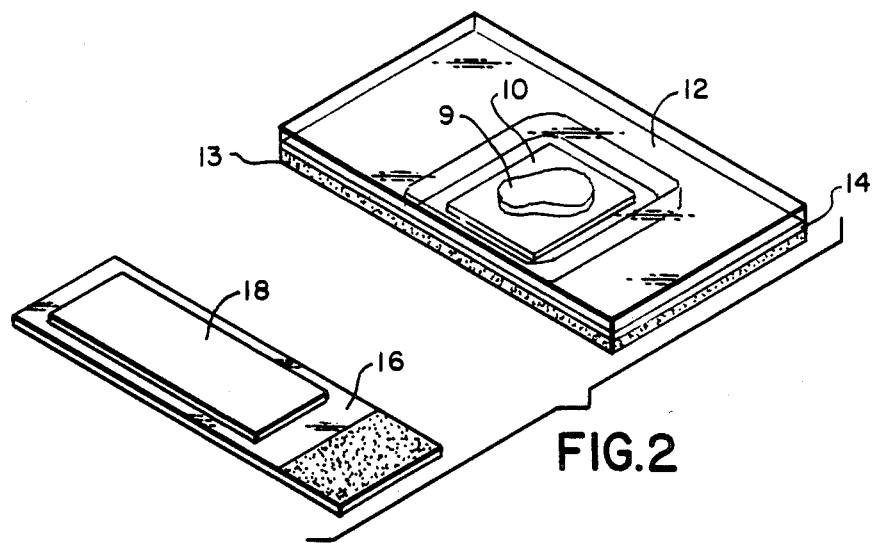
FIG. 2 is an isometric view of the substrate of FIG. 1 juxtaposed with a microscope slide.

Referring to FIG. 2, a microscope slide 16 is illustrated, which supports on its upper surface a pressure-sensitive adhesive layer 18. Layer 18 can be formed either of a heat-curable polymerizable material or a photopolymerizable material. Preferably, layer 18 is photopolymerizable, e.g., by exposure to U.V. light of wavelengths in the range of 320 nm-390 nm. FIG. 2 further illustrates the inversion of tape 12 so as to juxtapose specimen 9 and layer 18. Section and layer 18 are subsequently contacted. Preferably, a slight pressure is applied, e.g., manually. Also, such pressure can be applied progressively along the section 9, to insure a smooth contact therebetween and layer 18.

Layer 18 preferably is formed to have the characteristics of:

1. Being sufficiently tacky, when unpolymerized, to adhere to specimen 9.
2. Being polymerizable, so as to form a permanent bond between specimen 9 and slide 16.
3. Containing no curable components having diffusion coefficients large enough to permit diffusion of such components into tissue section 9 before polymerization of layer 18 as much as 1 micrometer in 30 minutes; it is evident that significant diffusion of any such components would, after curing, prevent penetration of processing reagents throughout specimen section 9 during subsequent processing.
4. Having a sufficiently high viscosity, so as not to flow into pores of specimen section 9 when contacted therewith and while pressure is being applied during the smoothing process; significant flow into the section would also intefere after curing, with subsequent processing.
5. When cured, being insoluble and unswellable in any of the reagents to which specimen section 9 is to be exposed during subsequent processing.
6. Having a refractive index compatible with the refractive indices of the unstained tissue, e.g., from about 1.53 to 1.57, and of the mounting medium conventionally used to envelop specimen section 9 on microscope slide 16.
7. When cured, being effective to strongly bond to both the bottom of section 9 and to the opposing surface of slide 16.

Figure 3A:
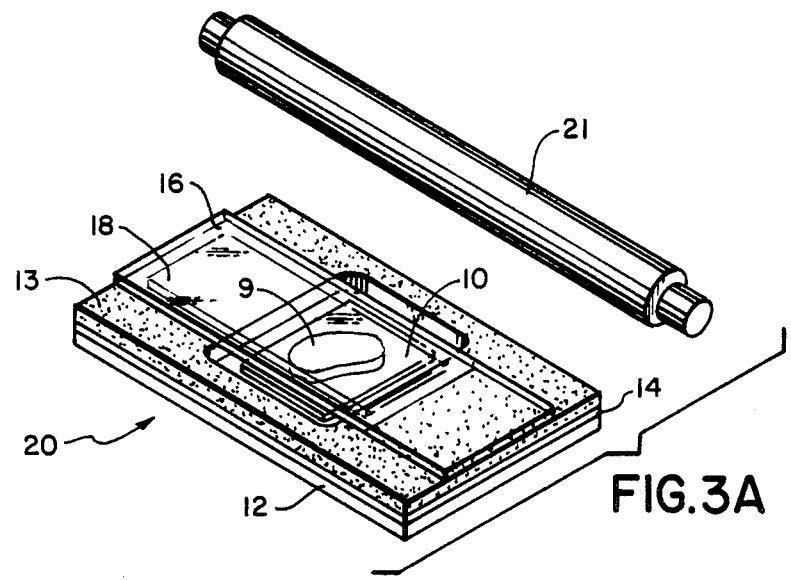
FIG. 3 is an isometric view illustrating the super-positioning of the substrate over the microscope slide, so as to laminate the thin tissue section therebetween.
FIG. 3B illustrates the removing of the substrate from over the microscope slide, to expose the thin tissue section bonded on such slide for further processing.

Accordingly, when section 9 has been contacted to layer 18 and smoothed, the resulting laminate 20 is exposed to U.V. light from source 21, as shown in FIG. 3A, for a time sufficient to completely polymerize layer 18 typically 3 minutes. Source 20 may be a 4-watt (or larger) black-fluorescent lamp (with phosphor-peak-light-output near 350 nm). At this time, layer 18 and the adhesive layer 14 on tape 12, which is unpolymerized, are firmly adhere to the interposed section 9.

Figure 3B:
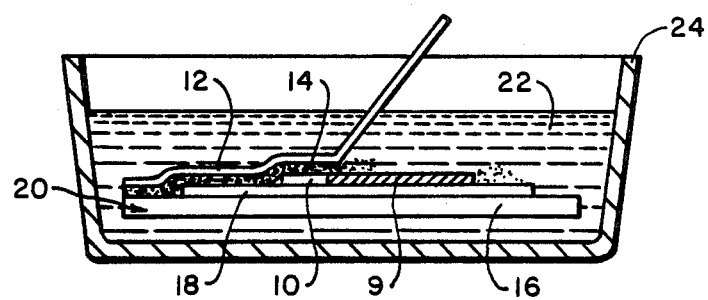

As shown in FIG. 3B, the laminate 20 is then immersed in a solvent solution 22, such as xylene, contained in beaker 24. Such immersion serves to rapidly soften the layer 14 on tape 12 and allows for a gentle manual peeling of tape 12 from over section 9 while laminate 20 is immersed in beaker 24. Exposed layer 14 and paraffin 10 dissolve as, or within one minute after, tape 12 is peeled away. The section 9 is now fully exposed. When layer 14 has been dissolved, the remaining laminate is ready for subsequent processing and section 9 is firmly bonded to the surface of slide 16. Also, it is evident that the solvent solution 22 may be selected, so as to be effective to dissolve both substrate 12 and adhesive layer 14, so as to avoid the need of peeling substrate 12, as described.

Preferably, the layer 18 on slide 16 consists of a mixture of very high molecular weight reactive oligomers (typically, each with two terminal acryl or methacryl groups). The high molecular weight assures high viscosity and low diffusion coefficient. If the molecular weight is too high, there will be insufficient tack. The acryl or methacryl groups permit radical-initiated polymerization to crosslink the oligomers into a highly insoluble polymer.

Typically, the mixture is composed of one oligomer with a cured refractive index of greater than 1.560 (e.g., an epoxyacrylate oligomer with many bisphenol A or other highly aromatic residues to raise the refractive index) and another with a cured refractive index less than 1.530 (e.g., a urethane acrylate oligomer). Both cured resins must be extremely resistant to xylene, alcohol and water. By mixing them in appropriate proportions, any desired cured refractive index, between 1.530 and 1.560, can be imparted to layer 18, when polymerized.

It is clear that other combinations of reactive oligomers and/or polymers with other initiators and solvents can be formulated by those skilled in the art to fill the requirements in the listed specifications. However, for a detailed description of compositions suitable for forming layer 18, reference is made to my U.S. Ser. No. 06,417,254, filed on even date herewith.

Matching of the refractive index of the layer 18 to the respective refractive indices of both section 9 and the mounting medium to be applied to envelop the section on slide 16 is critical. Unless such indices are properly matched, any surface imperfections on the cured upper surface of layer 18 for example, left by any texture on the now-removed adhesive layer 14 or paraffin 10, will be visible under microscopic examination as distracting, phase-contrast detail. Therefore, proper matching of such indices gives a very high quality finished microscope slide. The mounting medium for encapsulating specimen section 9 should preferably have a refractive index near 1.55, and layer 18, when cured, a refractive index of between 1.545 and 1.555.

Following peeling of tape 12, the now-exposed section 9 can be processed for storing and permanent encapsulation, according to conventional histological techniques. During such processing, section 9 is securely and permanently bound to slide 16 by now-polymerized layer 18, which neither affects nor is affected by exposure to such techniques. Such encapsulation process may be manually effected, for example, as fully described in McManus and Mowry above. Alternatively, a number of tissue sections 9, each supported on an individual slide 16, may be processed in automated fashion, for example, as clearly shown and described in an AUTOTECHNICON system as marketed by Technicon Instruments Corporation, of Tarrytown, N.Y., and described in their Technical Publication No. TA 1-0225-10, June 1977, pages 3-10 to 3-13.

Figure 4A:
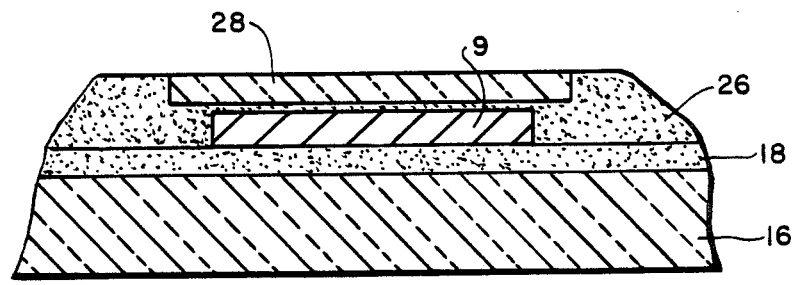
FIGS. 4A and 4B, respectively, illustrate the final mounting of a thin tissue section on a microscope slide, with and without a coverslip.
Figure 4B:
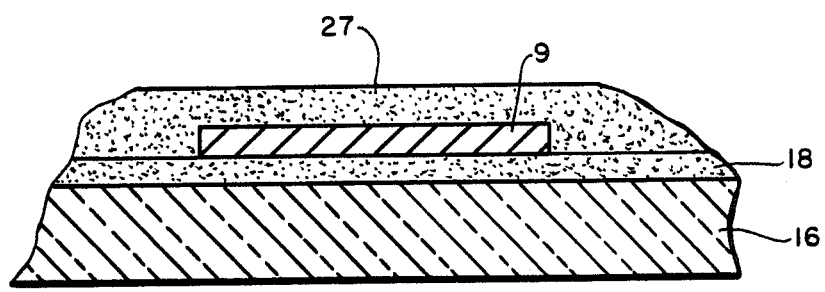

FIGS. 4A and 4B, each illustrates a completely mounted section, ready for microscopic viewing. FIG. 4A illustrates a section 9 mounted by conventional techniques; such section is covered with a mounting medium 26 and a coverslip 28 is located on such medium and over such section.

Alternatively, FIG. 4B shows the envelopment of a section 9 in a U.V. curable mounting medium 27, as results from the technique disclosed in U.S. Pat. No. 4,120,991. As shown, a coverslip is not provided. Rather, the upper surface of mounting medium 27 is formed so as to be optically flat.

For the purposes of this proces, the adhesive tape used to capture the sections must at least have an adhesive layer which is soluble in a solvent, such as xylene. A silicone rubber adhesive as used by Wedeen and Jernow referenced above is satisfactory for frozen sections, and an adhesive tape, like Permacel No. 925 is satisfactory for paraffin sectioning.

While several forms of a method for transferring a thin section of a tissue specimen to a microscope slide have been described, it will be apparent that such method is susceptible to various changes in detail without departing from the principles of the invention.

What is claimed is:

1. A process for transferring and mounting a thin section of a tissure specimen supported on a substrate by a first pressure-sensitive adhesive layer from said substrate onto a microscope slide having at least a portion of one surface coated with a second pressure-sensitive adhesive layer, comprising the steps of:

contacting said supported tissue section to said second layer to form a laminate comprising said substrate, said first layer, said tissue section, said second layer, and said microscope slide;

polymerizing said second layer, said second layer being formed of a polymerizable material (1) having acryl or methacryl functional groups, (2) containing no curable components having diffusion coefficients at the temperature of use large enough to permit signficant diffusion into said tissue section prior to or during polymerization and (3) having a viscosity at the temperature of use high enough to prevent significant flow into said tissue section prior to or during polymerization; and subsequently removing said substrate and said first layer to expose substantially the entire internal structure of said tissue section supported on said microscope slide for subsequent processing.

2. The process of claim 1, including the further step of processing said tissue section supported on said microscope slide, said processing step including the staining and mounting of said tissue to define a microscope-ready state.

3. The process of claim 1, wherein said removing step comprises the step of substantially completely dissolving said substrate and said first layer in said solvent.

4. The process of claim 1, wherein said substrate is flexible, and said removing step comprises the step of peeling said substrate and dissolving said first layer from over said tissue section.

5. The process of claim 1, wherein said polymerization step comprises the step of heat-curing said second layer.

6. The process of claim 1, wherein said polymerization step comprises the step of photopolymerizing said second layer.

7. The process of claim 1, comprising the further step of applying pressure to said laminate, prior to polymerization of said second layer, to insure adhesion of said tissue section to said second layer.

8. The process of claim 7, wherein said applying step comprises the step of smoothing said tissue section onto said first layer, to insure a uniform and complete contact therebetween.

9. The process of claim 1, including the further step of matching the refractive index of said second layer to that of said tissue section.

10. The process of claim 9, wherein said matching step comprises the step of forming said second layer to have a refractive index of from about 1.53 to 1.57, when polymerized.

11. The process of claim 1, further comprising the step of forming said second layer to have no curable components having diffusion coefficients large enough to permit diffusion into said tissue section of more than one micrometer in 30 minutes prior to or during polymerization.

12. The process of claim 1, further comprising the step of forming said second layer to have a viscosity large enough to prevent flow into said tissue section of more than one micrometer in 30 minutes prior to or during polymerization.

13. The process of claim 2, further comprising the step of forming said second layer to be unaffected by said processing step.

14. The process of claim 2, further comprising the step of forming said second layer so as to be inactive during said processing step.

15. The process of claim 1, wherein said removing step comprises the step of immersing said laminate in a solution in which said first layer is soluble, to facilitate removal of said substrate and said first layer from over said tissue section.

* * * * *